United States Patent [19]

Ip et al.

[11] Patent Number: 5,206,137
[45] Date of Patent: Apr. 27, 1993

[54] COMPOSITIONS AND METHODS USEFUL FOR GENETIC ANALYSIS

[75] Inventors: Nancy Y. Ip, Stamford, Conn.; Howard J. Baum, Stony Point, N.Y.

[73] Assignee: Lifecodes Corporation, Valhalla, N.Y.

[21] Appl. No.: 798,358

[22] Filed: Nov. 21, 1991

Related U.S. Application Data

[63] Continuation of Ser. No. 241,639, Sep. 8, 1988.

[51] Int. Cl.$^5$ .................. C12Q 1/68; G01N 33/48; G01N 33/566; C07H 15/12
[52] U.S. Cl. .................. 435/6; 435/320.1; 436/501; 436/94; 536/24.31; 935/77; 935/78
[58] Field of Search ............ 435/6, 320; 536/26–29; 436/501, 94; 935/77, 78

[56] References Cited

U.S. PATENT DOCUMENTS

| | | | |
|---|---|---|---|
| 4,348,477 | 9/1982 | Nakano et al. | 935/77 |
| 4,666,828 | 5/1987 | Gusella | 435/6 |
| 4,772,549 | 9/1988 | Frossard | 435/6 |
| 4,801,531 | 1/1989 | Frossard | 435/6 |
| 4,831,124 | 5/1989 | Paddock | 536/28 |

OTHER PUBLICATIONS

Jarman et al., EMBO 5(8):1857–1863 (1986).
Jeffreys et al., Nature 314:67–73 (7 Mar. 1985).
Goodbourn et al. PNAS (USA) 80:5022–5026 (1983).
Southern, E. M. (1975) "Detection of Specific Sequences Among DNA Fragments Separated by Gel Electrophoresis," J. Mol. Biol. 98:503–517.
Gusella, J. F., N. S. Wexler et al. (1983) "A polymorphic DNA marker genetically linked to Huntington's disease," Nature 306:234–238.
Orkin, S. H. (1986) "Reverse Genetics and Human Disease," Cell 47:845–850.
Baird, M., I. Balazs et al. (1986) "Allele Frequency Distribution of Two Highly Polymorphic DNA Sequences in Three Ethnic Groups and Its Application to the Determination of Paternity," Am. J. Hum. Genet. 39:489–501.
Nakamura, Y., M. Leppert et al. (1987) "Variable Number of Tandem Repeat (VNTR) Markers for Human Gene Mapping," Science 235:1616–1622.
Jeffreys, A. J., V. Wilson, S. L. Thein (1985) "Hypervariable 'minisatellite' regions in human DNA," Nature 314:67–73.

Primary Examiner—Amelia Burgess Yarbrough
Assistant Examiner—Stephanie W. Zitomer
Attorney, Agent, or Firm—Saliwanchik & Saliwanchik

[57] ABSTRACT

A method for obtaining polynucleotide sequences which are useful for detecting Variable Tandem Repeat polymorphism at multiple genetic loci and other genetic analyses under high stringency conditions (hence, with high specificity) is herein disclosed. Also disclosed are polynucleotide sequences and other compositions useful for DNA polymorphism and other genetic analyses.

7 Claims, 18 Drawing Sheets

Fig. 3A
Fig. 3B
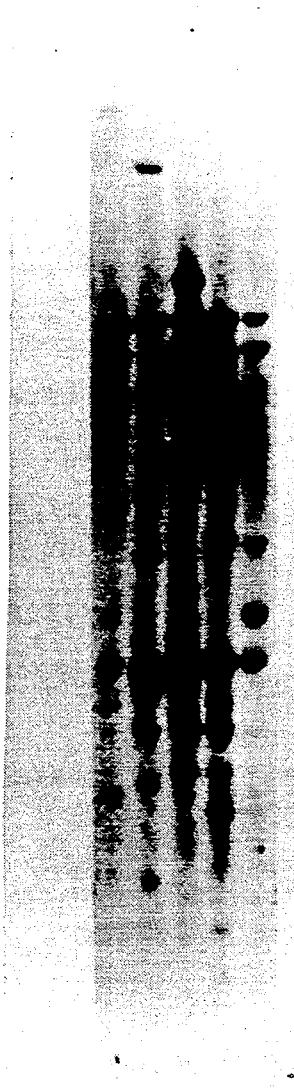
A
pAC 329
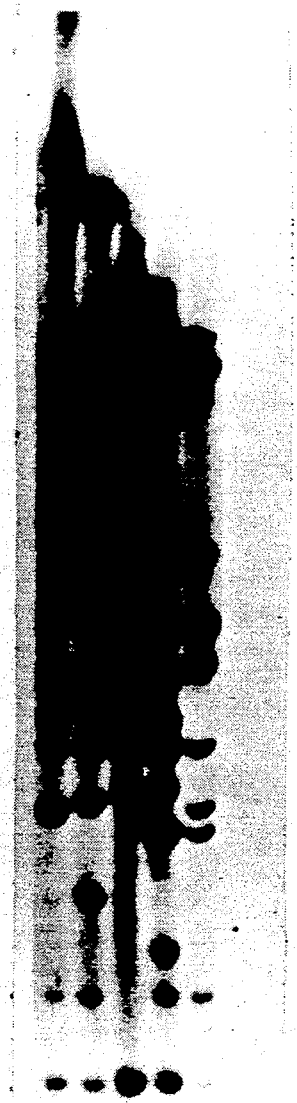
B
pAC 344

Band 1

Band 2

Band 3

Band 4 pAC 365 pAC 365

A
EcoRI-PstI

B
EcoRI-NcoI

Fig. 10A
Fig. 10B
A
B

Fig. 11A
Fig. 11B
A
B
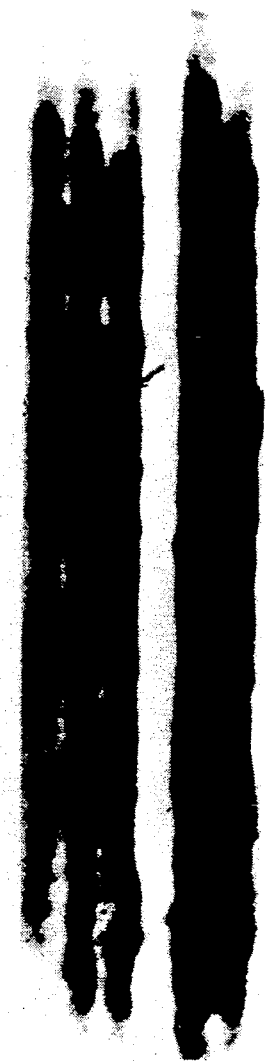
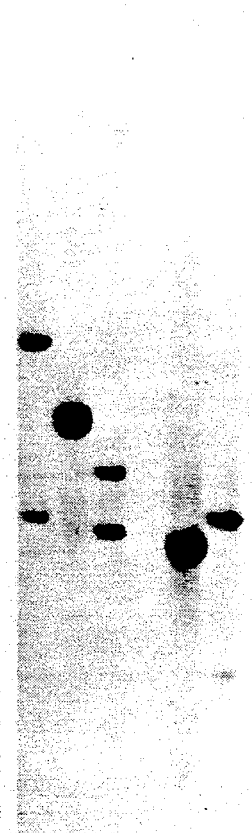

A. Blacks

B. Caucasoids

C. Hispanics

Size (Kbp)

Fig. 15A
Fig. 15B
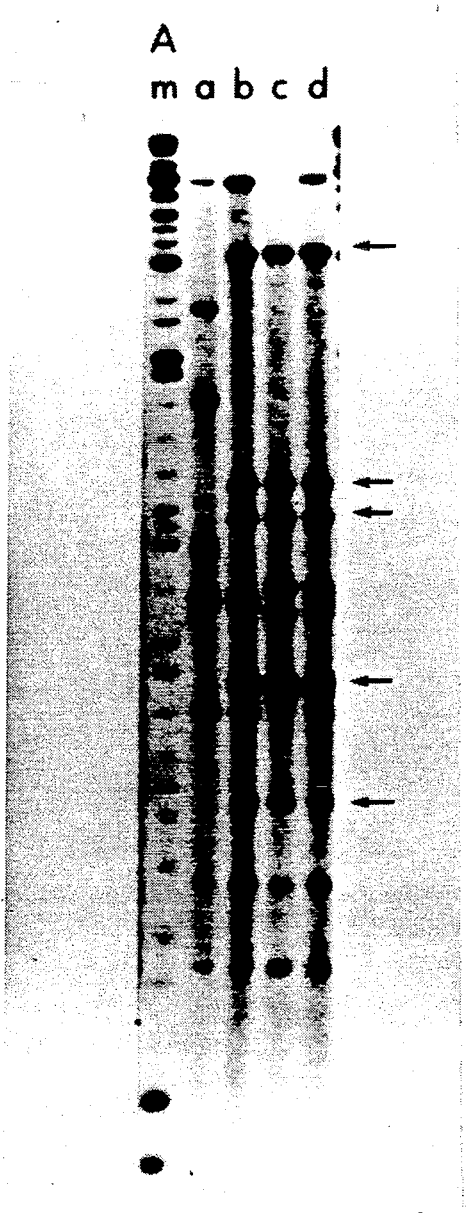
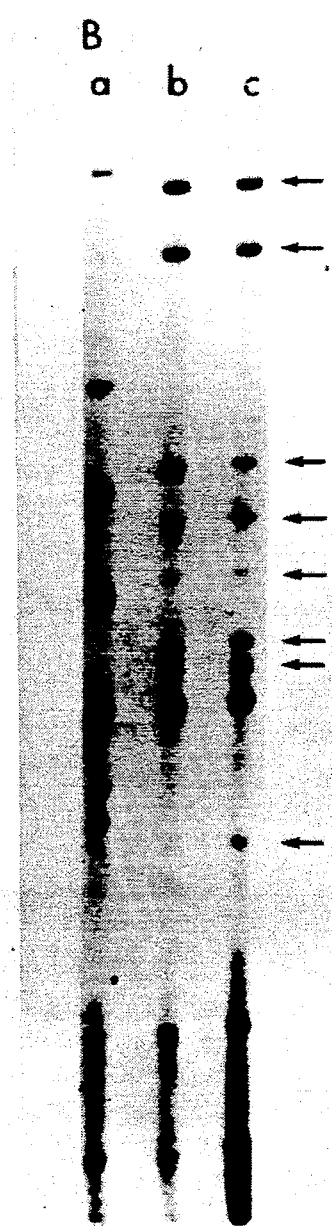

COMPOSITIONS AND METHODS USEFUL FOR GENETIC ANALYSIS

This application is a continuation of application Ser. No. 07/241,639, filed Sep. 8, 1988.

FIELD OF THE INVENTION

This invention relates to the field of molecular genetics. More specifically, this invention relates to polynucleotides useful for nucleic acid hybridizations, methods for producing these polynucleotides, and methods for applying these polynucleotides in genetic analysis.

BACKGROUND OF THE INVENTION

Double stranded DNA is the most common form of depository of genetic information of organisms. Double stranded DNA has two complementary strands. Each strand is a polynucleotide sequence and the base sequences on the two complementary strands form Watson-Crick base pairs. The duplex structure of DNA can be disrupted in a number of ways, for example, by heating a duplex DNA solution in a 0.1M NaCl to 100° C. for a few minutes. At this temperature, the two strands of duplex DNA separate. If the solution is gradually cooled, the two strands of duplex DNA can re-associate to reform the duplex structure.

The process of duplex formation from complementary polynucleotide or oligonucleotide sequences has been used advantageously for genetic analysis. Typically, a labeled polynucleotide or oligonucleotide sequence is used in a reassociation process whereby it forms a duplex structure with a substantially complementary sequence from a genetic source of interest. Because the labeled polynucleotide or oligonucleotide sequence is normally, though not necessarily, obtained from a source other than the source of interest, the process of association between complementary sequences has been known as nucleic acid hybridization, or just hybridization for short. The associational event provides genetic information about the source of interest through detection of the label on the labeled polynucleotide or oligonucleotide sequence. For this reason, the labeled polynucleotide or oligonucleotide sequence is called a probe. The label can be any suitable signal-generating moiety, and many such moieties are well known in the art.

Nucleic acid hybridization has been successfully applied in the study of DNA structure, gene purification, gene localization, the establishment of paternity and other familial relationship, genetic identity for forensic purposes, genetic identity of transplants, and detection and diagnosis of diseases and genetic traits.

One very powerful technique in the application of nucleic acid hybridization involves the fractionation of the complex genetic material to be analyzed prior to hybridization. E. M. Southern's procedure is the most celebrated and the most widely used of this genus. See Southern, J. Mol. Biol. 98: 503–517 (1975). Such a genetic analysis can reveal not only the presence or absence of complementary target nucleic acid sequences, but also the size of the restriction fragment(s) containing the target sequence. Genetic variations within a species may be reflected by variations among individuals in the size of the restriction fragments containing a particular target sequence. Conversely, genetic relatedness of a group of individuals may be reflected by a deviation from random variations that exist among unrelated individuals. This aspect of genetic analysis has been called Restriction Fragment Length Polymorphism (RFLP).

"Single-copy" DNA probes have been used in this approach with success. For example, certain genetic traits and disease states have been identified this way. See Gusella et al., Nature, 306: 234–238 (1983); Orkin, Cell 47:845–850 (1986).

The genetic information which can be adduced using "single-copy" DNA probes depends on the number of probes used, the number of genetic loci each probe is capable of detecting, the heterozygosities and the allele frequency of the relevant genetic loci. To date, "single-copy" DNA sequences are known to detect only a single locus per sequence. Moreover, heterozygosity of DNA in higher organism is low. In man, it is about 0.001 per base pair. Finally, most polymorphic states detected are only dimorphic (i.e. there are only two representational states: absence or presence of a relevant restriction site on the restriction fragment in question). As is often the case, critical individuals in a genetic analysis are homozygous, and the genetic analysis may be uninformative.

Genetic analysis in higher organisms has been simplified considerably by the availability of probes for hypervariable regions of genomic DNA. These hypervariable regions show multi-allelic variation and high heterozygosities. These regions also appear to be widely interspersed within the genome. In each case, the hypervariable region comprises a variable number of tandem repeats of a short sequence (thus, Variable Tandem Repeats or VTR), and polymorphism results from allelic differences in the number of repeats at a given locus. This type of polymorphism, a subclass of RFLP has been called VTR Polymorphism. It is believed that the variation in repeat number arises by mitotic or meiotic unequal exchanges or by DNA "slippage" during replication. Therefore, if genomic DNA is digested with a restriction endonuclease which does not cut within the repeat unit, and if a genetic locus encompasses a variable tandem repeat or VTR, allelic markers would exist for that locus. (It should be noted that the so-called repeat unit is a hypothetical consensus sequence, and any actual VTR sequence in the genome is really a string of short "core" sequences, each of which is very highly homologous, but usually not identical to the consensus sequence. Indeed, a "core" sequence may differ in length from the consensus sequence. The consensus sequence is derived from examining and "averaging" over a large number of "core" sequences. A "core" sequence is typically at least 70%, but often more than 70%, homologous to the consensus sequence.)

Jarman et al. have described a hypervariable region of DNA located 8-kb downstream of the human alpha globin complex. The EMBO J. 5: 1857–63 (1986). This hypervariable region is composed of an array of imperfect 17-bp tandem repeats, the number of which differs considerably (70–450) from one allele to another. Thus, this locus is highly polymorphic. Genetic polymorphism which reflects variations in the number of such tandem among individuals has been called Variable Tandem Repeat Length Polymorphism.

The VTR described by Jarman et al., supra, cross-hybridizes with other hypervariable genetic loci at low stringency. Thus a polynucleotide probe prepared from this region is potentially a very powerful probe, capable of probing many genetic loci in a single try.

A typical RFLP analysis involves digesting target genomic DNA with a restriction endonuclease, separating the digested DNA by gel electrophoresis, transferring the fractionated DNA in a denatured state to a binding surface, hybridizing the transferred DNA with a suitable probe, detecting the signals generated by the probe molecules which have become hybridized to the target DNA. The pattern of the signals generated would provide information about the target DNA. The pattern of signals can also be stored for later use, for instance, to determine or confirm an individual's identification (i.e., the pattern would be the individual's genetic fingerprint).

More commonly, two or more target DNA's are processed for RFLP analysis. Depending on the sources of the target DNA, the information generated by comparison of the patterns can be used immediately as in the case of genetic identity (e.g., identification of a suspect of a crime), or in the case where a high degree of genetic relatedness is present (e.g., paternity testing, sib analysis and the like). In other cases, the information derived from pattern comparison may form a part of a larger information-gathering effort. Pedigree analysis of distant relatives and correlation of a gene of genotype with a trait or medical condition are but two examples.

However the RFLP analysis is to be used, the pattern of signals is controlled in large part by the probe or probes used in the analysis. A polynucleotide probe may be useful for any of a number of features.

First, a probe may be able to detect polymorphism at a locus that other probes cannot detect. The locus may be particularly useful for genetic analysis in the general population because it has many evenly distributed alleles. Alternatively, the locus may be particularly useful for genetic analysis in a highly restricted segment of the population because it has a rare allele.

Second, a probe may be able to detect many loci simultaneously and unambiguously when a particular restriction endonuclease is used to digest the target DNA. In this connection, it is useful to note that certain restriction endonucleases may be preferred because of the history of the target DNA samples, e.g. forensic samples which have been exposed to the elements for an extended period of time.

Third, probes are often used in combination simultaneously because their resolving power may be compounded. Compounding is obtained when the signals produced by the several probes do not overlap and permit unambiguous assignment of each (or substantially each) signal to an allele of a locus. See, e.g., "The Application Of DNA-Print For The Estimation Of Paternity", Baird et al. in Advances in Forensic Haemogenetics 2: 354-358, Springer-Verlag, New York (1987).

How RFLP phenotypes can be practically applied for paternity and forensic determinations has been discussed in Baird et al., supra; Baird et al. (II), "The Application Of DNA-PRINT ™ For Identification From Forensic Biological Materials", in Adv. in Forensic Haemogenetics 2: 396-402, Springer-Verlag, New York (1987); and Baird et al. (III), Am. J. Hum. Genet. 39:489-501 (1986) and citations therein. These papers are hereby incorporated by reference.

Reference has been made earlier in the instant disclosure that hybrid formation can take place even where there is a certain degree of mismatch between a probe and its substantially complementary target sequence. This process is particularly important for the utility of multilocus probes. Such probes generally form well-matched hybrids with target sequences which originate from the same genetic locus as the probe, but they form less well-matched "cross-hybrids" with target sequences from other loci. As a result, the loci that can be analyzed with a given probe may vary significantly with the reaction (association and washing) conditions of the hybridization test. Thus, many loci are detectable under low stringency conditions, but only a single locus is detectable under high stringency conditions. Therefore, a polynucleotide sequence which is capable of probing multiple polymorphic loci even under high stringency conditions represents an additional bonus.

Strictly speaking, stringency of conditions has two components: conditions which govern formation of the hybrids and conditions which govern the stability of (the duplex structure of) the hybrids. Typically, however, a hybridization test is performed at low (or relaxed) conditions during the hybrid formation phase to speed up the process of association. Therefore, for the purpose of this application, stringency of conditions refer solely to conditions which govern the stability of the hybrids. (Of course, if a hybrid is not stable under a given set of conditions, it would not be formed in the first place under those conditions.)

The factors which govern the stability of a hybrid are many, including, but not limited to the temperature, the ionic strength, the molecular species of the salts used, the degree of modification or elimination of bases on a polynucleotide sequence, the degree and nature of mismatch, and the length and type of polynucleotides sequence. Variation in one factor may be compensated or aggravated by variations in other factors. These and other relevant facts are well known to a person of ordinary skill in the art of molecular genetics.

For the purpose of this invention, low stringency conditions mean an aqueous environment containing about 2 X SSC at about 50°-65° C., or the equivalents thereof; and high stringency conditions mean an aqueous environment containing about 0.1 X SSC or less at about 65° C., or the equivalents thereof. [For formulation of 1 X SSC, see Example 3 in Section 6 below].

For the purpose of this invention, a "discrete polynucleotide sequence or subsequence" means a polynucleotide sequence or subsequence of greater than 15 nucleotides, but preferably greater than 50 nucleotides, and very preferably greater than 100 nucleotides; and a polynucleotide means a chain of about 15 nucleotides or more, and embraces the upper range of what sometimes passes as oligonucleotides.

Many "single copy" DNA probes are known in the art. These probes do not relate closely to the present invention because their utility is generally (1) limited to providing genetic information at a single locus; and (2) limited to detecting polymorphism caused by alteration of a restriction site in the neighborhood of the target genomic sequences. The polymorphic probes of the present invention are of the VTR type and do not suffer from these limitations.

Polymorphic probes of the VTR type have also been described. However, the hybrids formed between a VTR probe and its target genomic sequences tend to be stable only under low to moderate stringency conditions, except for hybrids between the probe and target sequences from a single genetic locus. See Nakamura et al. (I), Science 235: 1616-1622 (1987); Jeffreys et al., Nature 314:67-73 (1985). The exceptional hybrids are stable even under high stringency conditions, possibly reflecting the fact that the probes originated from this locus.

Sometimes a genetic locus detectable with a VTR type probe may be very large, spanning several hundred kilobases. In a restriction fragment length polymorphism analysis of such a large locus, a VTR can yield many polymorphic bands under high stringency conditions. However, the information which can be derived from such an analysis remains confined to the one locus. In fact, VTR probes for loci of this kind have disadvantages. First, recombination within the large locus (which is expected to be more frequent than a similar but smaller locus) can complicate data analysis. Second, to obtain more extensive information than is obtainable from only a single locus, two or more probes are preferably used in combination. The multiplicity of non-informational bands from the large locus may obscure bands detected by other probes used in combination, thereby making data analysis very difficult. The alternative to using probes in combination would be more costly multiple analyses of restriction fragment length polymorphism. Therefore, the difference between a probe for a large single locus and a probe for multiple loci is substantive, and not merely semantic.

BRIEF SUMMARY OF THE INVENTION

The subject invention concerns the following:
(1) polynucleotide sequences useful for detecting polymorphism in a species of organism of interest, or a subpopulation thereof;
(2) a polynucleotide sequence useful for detecting polymorphism at multiple genetic loci, and characterized by its ability to form hybrids with restriction fragments of DNA, of 7.1, 6.2, 4.4, 4.2, 4.1, 3.7, 3.6, 2.6 and 2.2 kilobases, produced by PstI digestion of genomic DNA extracted from K562 cells;
(3) a polynucleotide sequence useful for detecting polymorphism at multiple genetic loci and capable of forming hybrids with genomic DNA fragments produced by complete digestion of Caucasoid, American Black or Hispanic genomic DNA with the restriction endonuclease PstI of approximate allelic lengths and allelic frequencies as given in Table 2;
(4) a polynucleotide sequence useful for detecting polymorphism at multiple genetic loci with high specificity, i.e., the polynucleotide sequence forms hybrids with genomic sequences at multiple genetic loci which remain stable even under high stringency conditions;
(5) a method for determining or obtaining a polynucleotide sequence useful for detecting polymorphism at multiple genetic loci with high specificity;
(6) the use of the above-described polynucleotide sequence as a probe for polymorphism;
(7) the use of the above-described polynucleotide sequence as a probe for polymorphism at multiple genetic loci;
(8) a method of genetic analysis comprising:
  (a) digesting a DNA sample with a restriction endonuclease;
  (b) separating the DNA restriction fragments according to size by electrophoresis;
  (c) transferring the separated DNA to a binding surface;
  (d) hybridizing the transferred DNA with a polynucleotide probe labeled with a signal-generating moiety, wherein the polynucleotide probe is a polynucleotide probe of the present invention; and
  (e) detecting the signal generated; whereby the pattern of signals generated provides information about the composition of the DNA sample; and
(9) recombinant vectors and cells useful for producing polynucleotides of the invention.

BRIEF DESCRIPTION OF THE FIGURES

FIG. 3 shows the results of a hybridization blot where a panel of PstI digested human genomic DNAs from five unrelated individuals was hybridized with either the insert of pAC329 (FIG. 3A), or the insert of pAC344 (FIG. 3B).

FIG. 5 shows the results of a hybridization blot where PstI digested human genomic DNA was probed with RsaI restriction fragments of the inserts of pAC329 and pAC344.

FIG. 11 shows the results of hybridization blots where PstI digested human genomic DNA was probed with the 1.35 kbp human insert of pAC256, and washed under either low stringency conditions (FIG. 11A), or high stringency conditions (FIG. 11B).

FIG. 15 shows the results of hybridization blots for genetic identification purposes. pAC365 insert was used as probe in a paternity test (FIG. 15A), and a forensic test (FIG. 15B).

DETAILED DESCRIPTION OF THE INVENTION

Figure 1A:
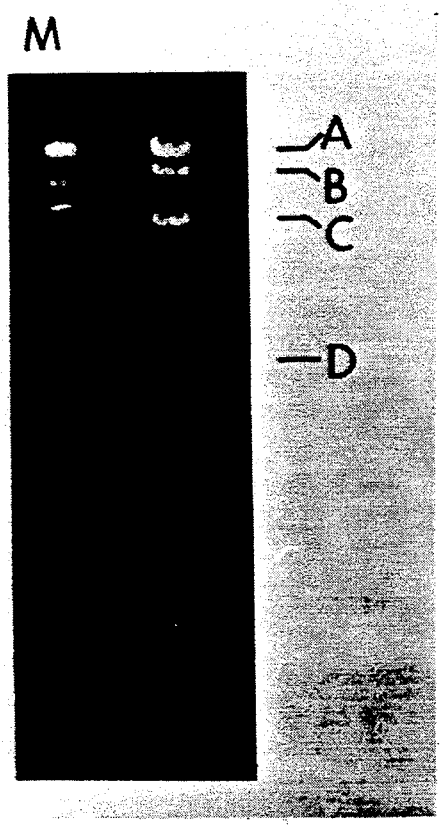
FIG. 1 shows the electrophoretic pattern of restriction fragments of DNA's from recombinant lambda phage 19 which was digested with EcoRI (FIG. 1A), and the results of a Southern hybridization blot when the DNA fragments were transferred and probed with oligo-5'-CCCCCCGTGTCGCTGTT-3' (FIG. 1B).

One embodiment of the instant invention is a method to obtain polynucleotide sequences useful for detecting polymorphism in a species, or a subpopulation thereof. A library of genomic DNA digested with one or more restriction endonucleases and cloned in a suitable recombinant vector is screened with a polynucleotide probe which comprises a string of "core" sequences (hereinafter "screening probe"). This string of "core" sequences can, but need not be, a monomer, an oligomer or a polymer or a mixture of oligomers and polymers of a consensus sequence or "core" sequence of a VTR. Preferably, the screening probe is a mixture of oligomers of a consensus sequence, because a short consensus sequence can be easily synthesized chemically in large amounts and ligated to form a mixture of oligomers. In a preferred embodiment, the consensus sequence is 5'-CCCCCCGTGTCGCTGTT-3'.

For the purpose of generating a genomic library, it is preferred that the restriction endonuclease digestion of genomic DNA be incomplete. One reason is that many genomic VTR sequences may otherwise evade detection. This would be so if the relevant restriction endonuclease cuts within the VTR sequences, and the bulk of the VTR sequences will be in relatively small pieces. The smaller the pieces, the greater the number of recombinant molecules which must be studied so that the human genome will be covered. For the same reason, it is preferred that a recombinant vector which can accommodate large DNA insert be used. Finally, where the recombinant vector has a restricted cloning range, incomplete digestion of the genomic DNA would also tend to avoid under-representation in the library of completely digested products which are smaller than the preferred cloning sizes.

The recombinants which react positively with the screening probe in a hybridization test (hereinafter "positive recombinants") are selected for further examination. In a preferred embodiment, the recombinants are bacteriophages. The standard method of "phage lifts" can be used to identify the recombinants containing DNA inserts which hybridizes to the probe. See Maniatis et al., Molecular Cloning: A Laboratory Manual, Cold Spring Harbor Laboratories, Cold Spring Harbor, N.Y., (1982). Briefly, a portion of a phage plaque is transferred to a nylon membrane where the DNA of the phage is immobilized and probed. Many plaques can be transferred in a single lift; moreover, the position of a plaque on the growth plate is in a one-to-one correspondence with the position on the membrane, thus permitting identification of the plaques which give rise to positive results in a hybridization test with the probe. Obviously, many variations of this basic technique can be designed with other cloning and/or transfer and/or identification systems.

Once the positive recombinants have been identified, they can be subjected to tests which prove or disprove their utility. They are used as probes in hybridization tests against genomic sequences of a species of organism of interest, or a relevant subpopulation thereof. While the present invention broadly encompass eukaryotic organisms, one of the more commercially significant use is that of probing mammalian genomes, particularly, the human genome. In any case, it is very highly preferred that the probe sequences of the present invention be derived from the same species of organisms as the genetic materials which are to be tested in a hybridization test. Thus, for applications of human genetic analysis, the starting library should preferably be a human genomic library. To avoid verbosity, the embodiments of this invention are described as if they apply to humans specifically. The present invention is not so limited, and is to be construed to be applicable generally to mammals and other eukaryotes.

The useful positive recombinants are those which can detect Variable Tandem Repeat Length Polymorphism in humans, at multiple loci, and under high stringency conditions. Genomic DNAs from family members are separately digested with a restriction endonuclease, the digests are separately subjected to size fractionation by, for example, electrophoresis, and the fractionated restriction fragments are prepared for hybridization in any standard method. Positive recombinants or the human sequences or discrete polynucleotide subsequences inserted therein (jointly and severally "test sequences") are used to probe the restriction digests. Preferably, a single test sequence is used at a time. However, several sequences can be grouped together in preliminary tests to determine whether the group as a whole contains any useful sequences.

The hybridization "banding" pattern for each individual member is determined. In particular, the sizes of restriction fragments which hybridize to the test sequences are determined. The segregation scheme of each band within a family or, more commonly, a number of families will inform as to the nature of the genetic locus (loci) being detected. The nature of a genetic locus includes, but is not limited to, the following: 1. Mendelian or non-Mendelian segregation; 2. phenotype and frequency of alleles (reflected by the size of restriction fragments produced by the restriction endonuclease used to digest the genomic DNA, and the frequency of occurrence in a population); 3. linkage to another locus (reflected by co-segregation with other bands). If the test sequence detects multiple bands which segregate independently, it is capable of detecting multiple genetic loci. If test sequence detects bands of a locus which bands represent different-sized fragments among different individuals, it is capable of detecting polymorphism in that polymorphic locus. The determination of the nature of the locus (loci) detected by a test sequence from the segregation scheme is a straight forward application of classical genetics, and is well within the command of a person of ordinary skill in the art of molecular genetics. The size of families, and the number of families needed to provide sufficient information to work out the segregation scheme would vary with the number of genetic loci being detected by the test sequence, the number of alleles in these loci, and the frequency of each allele. An ordinarily skilled artisan would also know how to determine the number and size of families to be studied.

Another embodiment of the instant invention is the test sequences which can detect polymorphism in an species of organism of interest, or a subpopulation thereof (hereinafter "useful test sequence").

In another embodiment of the instant invention, useful test sequences are cloned in recombinant vectors. In another embodiment, the recombinant vectors comprising the useful test sequences are harbored in a cell. Molecular cloning and transformation methods are well known in the art.

In a preferred embodiment, the useful test sequences are such that the hybrids formed between the test sequence and genomic sequences from at least two genetic loci are stably associated under high stringency conditions.

Because the segregation scheme is both lengthy and expensive to workout, it is sometimes preferable to defer the study of segregation until a test sequence has been better characterized. Thus, it may be preferable to modify the method described hereinabove, namely, to use instead of genomic DNAs from members of families, merely genomic DNAs from random, unrelated individuals. If the banding pattern appear to vary from individual to individual, the test sequence is presumptively treated as being useful as a polymorphic probe. If the number of bands detected in each of several individuals is significantly greater than one or two, the test sequence is presumptively treated as being useful as a multi-locus probe.

The presumptively useful test sequence is analyzed, and less desirable sequence(s) are removed to produce an improved test sequence. For example, a test sequence may comprise a subsequence which is polymorphic as well as a subsequence which is non-polymorphic in the relevant population. The presence of non-polymorphic bands yields no useful genetic information about a human individual, but can interfere with genetic analysis by, for example, obscuring a partially or totally informational band detected by a second probe used in combination with the test sequence. Another example is where the test sequence comprises a subsequence which is a highly repetitive sequence in the human genome. An example of a highly repetitive sequence is the "Alu sequence". See Houck et al., J. Mol. Biol. 132: 289–306 (1979). Presence of such highly repetitive sequences in a probe often cause a high non-informational background signal in a hybridization blot. This background signal can be avoided by eliminating the highly repetitive sequence component from the test sequence. See, for example, Sealey et al., Nuc. Acids Res., 13: 1905–1922 (1985).

Still another example is where the test sequence comprises a first subsequence which delivers only a small signal in a hybridization blot relative to the signal delivered by a second subsequence. Here, it may be more advantageous to eliminate the first test subsequence so that a more "cost-effective" probe which delivers a higher signal on a per nucleotide basis may be produced. A more specific example of this type is where the first subsequence is a "single-copy" sequence, and the second subsequence is a Variable Tandem Repeat Sequence. On a per nucleotide basis, the second sequence delivers more signal whenever there are more than a single copy at a genetic locus.

Discrete polynucleotide subsequences may be obtained from a test sequence in a number of ways, and are well within the capability of an ordinarily skilled artisan. For example, one end of the test sequence may be progressively removed by an exonuclease or S1 enzyme, while the other end is being protected. Another example is digestion with a restriction enzyme. Other methods of obtaining subsequences are within the contemplation of the present invention.

After the less desirable subsequences have been eliminated from a test sequence, the remaining portion of the test sequence is used in familial tests for the determination of the nature of the genetic locus (loci) which it is capable of detecting as described above.

Finally, nearby genomic sequences (including nearby VTR sequences) may be reached by chromosome walk.

As discussed in the Background section of this application, duplex formation and stability depend on substantial complementarity between the two strands of a hybrid, and a certain degree of mismatch can be tolerated. Therefore, whenever a test sequence obtained as described hereinabove has been determined to be useful in probing target polynucleotides of interest, mutations (both single and multiple), deletions, insertions of the useful test sequence, and combinations thereof, wherein said mutations, insertions and deletions permit formation of stable hybrids with said target polynucleotide of interest, are part of the present invention. Mutations, insertions and deletions can be produced in a given polynucleotide sequence in many ways, and these methods are known to an ordinarily skilled artisan. Other methods may become known in the future. The known methods include, but are not limited to: 1. determining analytically the sequence of a test sequence of the present invention, synthesize chemically or otherwise an artificial sequence which is a mutation, insertion or deletion of the test sequence; 2. using a test sequence of the present invention to obtain via hybridization a genomic sequence or otherwise which is a mutation, insertion or deletion of the test sequence; and 3. mutating, inserting or deleting a test sequence in vitro or in vivo.

It is important to note that the mutational, insertional, and deletional variants generated from a given test sequence may be more or less efficient than the test sequences, in the sense that (a) more or fewer genetic loci may become detectable, (b) more or fewer alleles of a particular locus may become detectable, (c) more or less stable under stringent hybridization conditions, and (d) any combination of the above. Notwithstanding such differences in efficiency, these variants are within the scope of the present invention.

In another embodiment of the present invention, the useful test sequences described hereinabove are used for genetic analysis, (i.e., used as probes), including but not limited to analysis of genetic identity, relatedness or alteration. In one preferred embodiment, the method of genetic analysis comprises:

(a) digesting a DNA sample with a restriction endonuclease;

(b) separating the DNA restriction fragments according to size by electrophoresis;

(c) transferring the separated DNA in a state suitable for hybridization to a binding surface;

(d) hybridizing the transferred DNA with a useful test sequence labeled with a signal-generating moiety, and (e) detecting the signals generated; whereby the pattern of signals generated provides information about the composition of the DNA sample.

This and other embodiments of the present invention involve the use of useful test sequences as probes in methods of genetic analysis.

EXAMPLES

Following are examples which illustrate procedures, including the best mode, for practicing the invention. These examples should not be construed as limiting. All percentages are by weight and all solvent mixture proportions are by volume unless otherwise noted.

Example 1

Detection Of Genomic Sequences Which Hybridize With Oligomers Of A Consensus Sequence Of A VTR Human genomic DNA incompletely digested with the restriction endonuclease EcoRI was cloned into the bacteriophage lambda Charon 30. Restriction fragments ranging from 4.5 kbp to 17.5 kbp can be cloned into this vector. Gene 12: 301–309 (1980). About 5000 phage plaques were screened according to the method of Maniatis et al., supra, at page 321. Oligomers of 5'-CCCCCCGTGTCGCTGTT-3', the 17-base consensus sequence of VTR at the 3' end of the human alpha globin complex, with an average length of 200–300 bases, were used to screen the phage "lifts".

Example 2

Analysis Of Human Sequences In Recombinant Phages Whose DNA Hybridizes With Oligomers of VTR Consensus Sequence A number of recombinant phages whose DNA hybridized with oligo-5'-CCCCCCGTGTCGCTGTT-3' were analyzed. The results obtained with Phage 19 are presented below. DNA from Phage 19 was extracted and digested with the restriction endonuclease EcoRI. The digests were subjected to electrophoresis in an agarose gel. The electrophoretic pattern obtained is shown in FIG. 1A. Lane M contained bacteriophage lambda HindIII fragments as molecular weight markers. Bands A and B are the arms of the cloning phage vector. Bands C and D are human genomic sequence inserts.

Figure 1B:
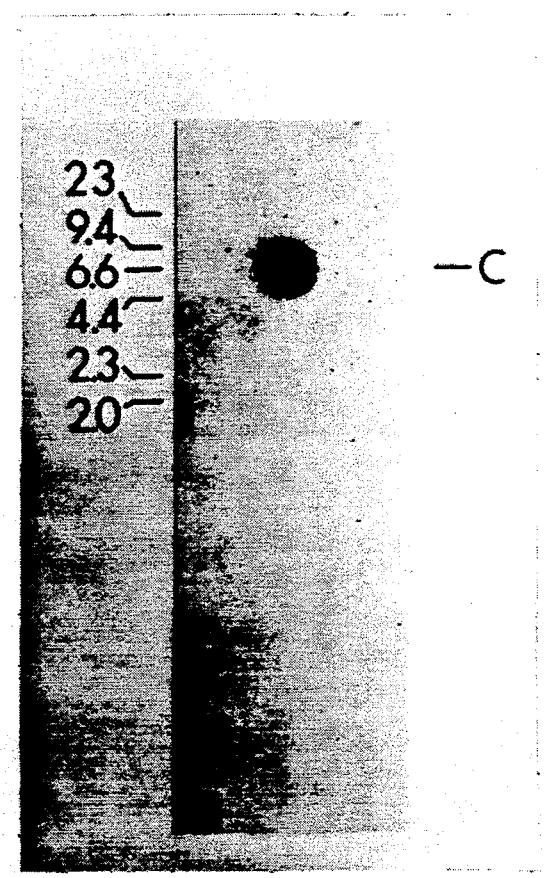

The DNA fragments in FIG. 1A were transferred to a nylon membrane, and probed with oligo-5'-CCCCCCGTGTCGCTGTT-3' according to the procedure of Southern, supra. FIG. 1B shows the results of the hybridization blot. The numbers on the side of the Figure state the molecular weight in kilobase pairs. Only the larger human insert band, i.e., Band C was detected. See FIG. 1B. Therefore, only Band C contained human DNA which is homologous with oligo-5'-CCCCCCGTGTCGCTGTT-3'.

Example 3

Human Genomic Sequence Inserts from Phage 19 As Polymorphic Probes

DNAs from Bands C and D of FIG. 1A, representing the human genomic sequence insert in Phage 19, were extracted separately. They were used separately in the Southern format to probe human genomic DNAs from 4 unrelated individuals.

The target human sequences were restriction fragments produced by digestion with one of the following restriction endonucleases: PstI, HinfI, HindIII, EcoRI, TaqI, MspI, PvuII, RsaI, and BstNI.

The following experiment and results were representative. 5 ug of PstI digested DNA from each of 4 individuals were electrophoresed and blotted onto a nylon membrane. Nylon membranes were prepared in duplicate. Either [$^{32}$P]-labeled DNA from Bands C of FIG. 1A, or [$^{32}$P]-labeled DNA from Band D of FIG. 1A was mixed with excess unlabeled total human genomic DNA, and used to probe the target sequences on the membranes. Radioactive labeling was achieved by random 6-mer primed enzymatic synthesis, using radioactive precursors as substrates. However, other methods of labeling would also work as well. Total unlabeled human genomic DNA was added as a precautionary measure. It was known that the human genome contains widely dispersed highly repetitive sequences such as the Alu sequences. If the human insert in Phage 19 contained these and/or similar highly repetitive sequences, such repetitive sequences would produce a heavy background signal over the entire area on the blot where human target DNA could be found. The introduction of total human genomic DNA would serve to suppress this background signal. Sealey et al., supra.

The hybridization was carried out at 65° C. in 5 X SSPE, 1–2% SDS (sodium dodecylsulfate), 0.5–1 mg/ml heparin. The blot was washed in 0.1 X SSC, 2.5 mM sodium phosphate, 1% SDS at 65° C. [1 X SSPE 0.16M NaCl, 0.01M sodium phosphate, and 1 mM ethylenediaminetetraacetic acid. 1 X SSC=0.15M NaCl, 0.015M sodium citrate.]

Figure 2A:
FIG. 2 shows the results of 2 hybridization blots. PstI digested human genomic DNA from a group of 4 unrelated individuals were probed with either DNA from Bands C of FIG. 1A (FIG. 2A), or DNA from Band D of FIG. 1A (FIG. 2B).
Figure 2B:
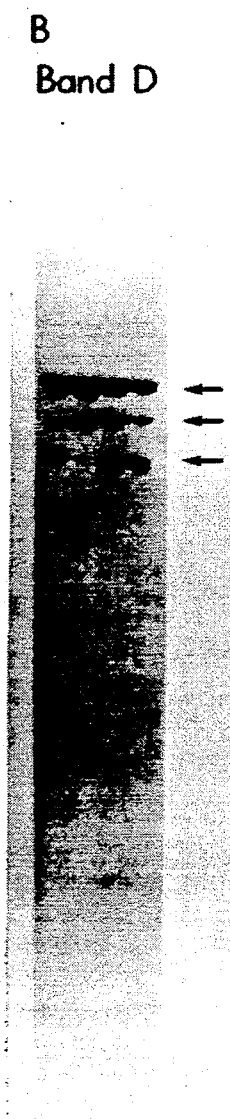

FIG. 2 shows the results of these hybridization blots. Band C DNA was used in FIG. 2A. Band D DNA was used in FIG. 2B. In FIGS. 2A, the lane marked M contained lambda HindIII fragments as molecular weight markers, and the remaining four lanes contained PstI digested DNA from unrelated individuals. The same preparation of human DNAs was used in FIG. 2B.

An average of about 7–10 bands were detected in each individual when Band C DNA was used as probe. See FIG. 2A. By contrast, Band D DNA could detect only a subset of the bands. See FIG. 2B. The subset, indicated by the arrows, were present in all 4 unrelated individuals and would therefore appear to be non-polymorphic. The other bands were present in some but not all individual, and therefore, polymorphic. See FIG. 2A. The fact that these polymorphic bands relate to multiple loci was confirmed in Example 10.

Band C human insert DNA was also able to detect multiple polymorphic loci when human genomic DNAs were digested with HinfI, HindIII, EcoRI, TaqI, MspI, PvuII, and RsaI. However, polymorphism was not detected when the human genomic DNA was digested with BstNI. Because genetic variations other than the VTR type are rare in man (about 0.001 per base pair), the probability that a non-VTR type polymorphism, i.e., a polymorphism caused by alterations in restriction sites in the neighborhood of the target sequence, would be revealed by at least seven restriction enzyme digestion is vanishingly small. Correlatively, the evidence is overwhelming that Band C DNA is detecting a VTR type polymorphism. The BstNI data is consistent with the hypothesis that the VTR being detected here has an internal BstNI site. The results of Example 6 as well as partial sequencing data support this hypothesis.

Therefore, Band C DNA, but not Band D DNA is useful as a multi-locus, polymorphic probe.

Example 4

Cloning Of The Human "polymorphic Probe" Sequence From Phage 19

DNA in Band C of FIG. 1A, representing part of the human sequence insert in Phage 19 was extracted, and cloned into Bluescript, which is a trademarked cloning vector of Stratagene, San Diego, Calif. 92121. Bluescript is a derivative of M13 as well as of pBR322, and is about 3 kbp long. The EcoRI insertion site was used. Several Bluescript recombinants containing Band C human DNA were obtained.

Two clones designated pAC329 and pAC344 were used to probe a panel of human genomic DNAs. DNA from 5 unrelated individuals were digested with PstI and two duplicate filters were prepared for the Southern procedure. The hybridization conditions were the same as described in Example 3. FIGS. 3A and 3B show the results obtained when the inserts of pAC329 and pAC344 were used as probes respectively. It is readily seen that the same pattern (of multiple bands) were obtained. However, the pAC344 insert is slightly longer, and more sensitive, i.e., produces a stronger signal under comparable conditions.

A third Bluescript recombinant was able to detect only non-polymorphic bands, i.e. the banding patterns are identical in several unrelated individuals. (Data not shown).

Band C appears to have more than one species of DNA sequences each approximately 5 kbp long. This is consistent with the preferred cloning size of the Charon 30 vector (see Example 1 above).

This Example shows that both pAC329 and pAC344 are useful as multi-locus, polymorphic probes.

Example 5

Figure 4:
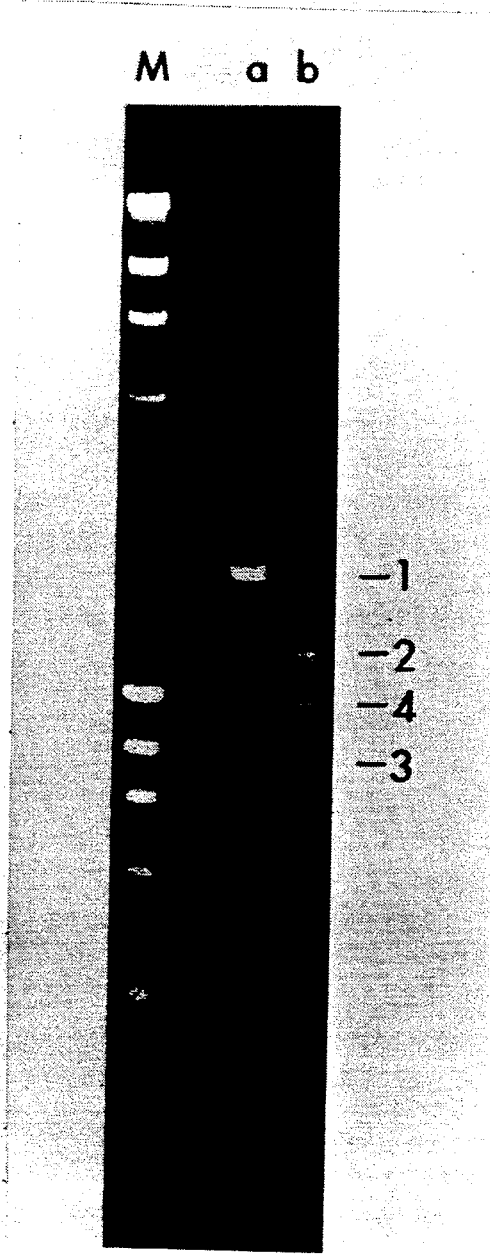
FIG. 4 shows the electrophoretic patterns of the RsaI digests of the inserts of pAC329 and pAC344.

Analysis Of Human DNAs In pAC329 And pAC344 pAC329 DNA was digested with EcoRI and the approximately 5 kbp human DNA insert was isolated. The same was done with pAC344 DNA. The purified inserts were further separately digested with RsaI, and the products of the restriction digest was electrophoresed in a 1% agarose gel. The electrophoretic pattern is shown in FIG. 4. Lane (M) contained molecular weight markers (lambda HindIII and phi-x HaeIII fragments). Lane (a) contained restriction fragments from the insert of pAC329; and lane (b) contained those from the insert of pAC344.

DNA from each of the four marked bands shown in FIG. 4 was isolated and used to probe unrelated, human genomic DNAs in the Southern format. The hybridization conditions were as described in Example 3, except that unlabelled human genomic DNA was not present in the probe mix. Relevant results of hybridization blots against PstI digested human genomic DNA are shown in FIG. 5. The general conclusion is that DNA from each of Bands 1, 2, 3 and 4 are useful as multi-locus, polymorphic probes.

Figure 5A:
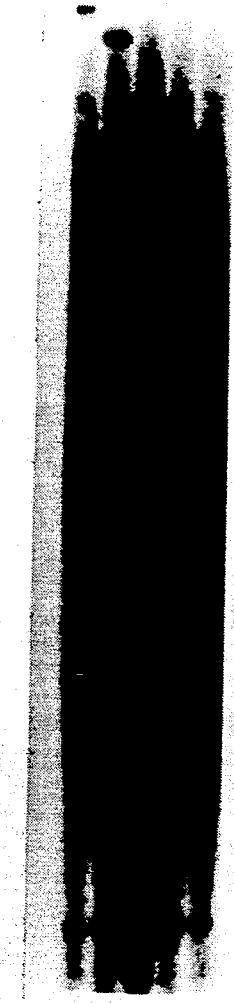
FIGS. 5A, 5B, 5C and 5D shows the results when Band 1, 2, 3 or 4 of FIG. 4 respectively was used as probe.

FIG. 5A shows the hybridization results when DNA from Band 1 of FIG. 4 was used as the probe. Under the above-indicated hybridization conditions, if the probe contained highly repetitive sequences such as the "Alu sequences", a background signal in addition to any specific bands might be produced, because the probe would have hybridized to homologous highly repetitive sequences which are widely dispersed throughout the human genome. Such background signal is indeed indicated in FIG. 5A.

Figure 5B:
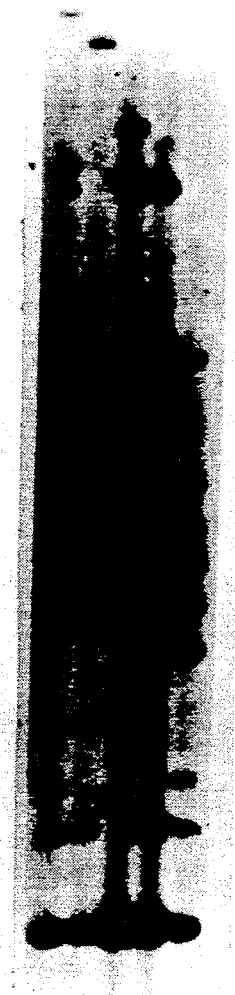

FIG. 5B shows the hybridization results when DNA from Band 2 of FIG. 4 was used as the probe. Otherwise, the target and the hybridization conditions were identical. In contrast with FIG. 5A, background signals which are indicative of the presence of highly repetitive sequences in the probe are not as evident here.

Figure 5C:
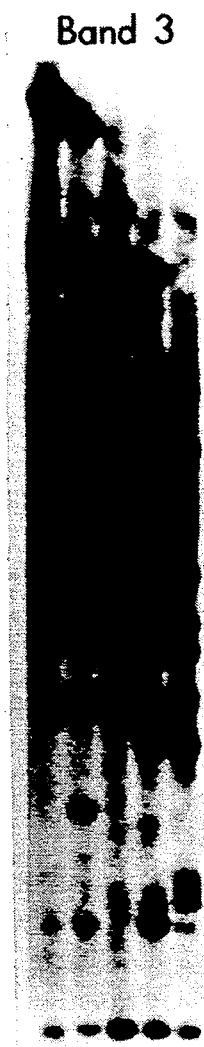
Figure 5D:

Similarly, FIGS. 5C and 5D show the respective results when DNA from Bands 3 and 4 were used as the respective probes. FIG. 5D shows rather less background signal than FIG. 5C.

This Example shows that the subsequences of pAC329 and pAC344 represented by Bands 2 and 4 are improvements over pAC329 and pAC344 as multilocus, polymorphic probes.

DNA from Band 4, i.e., the second largest restriction fragment from RsaI digestion of the human DNA insert in pAC344 was cloned into the SmaI insertion site of Bluescript by "blunt end cloning". The recombinant molecule has been designated pAC365.

Example 6

Analysis Of pAC365

Figure 6:
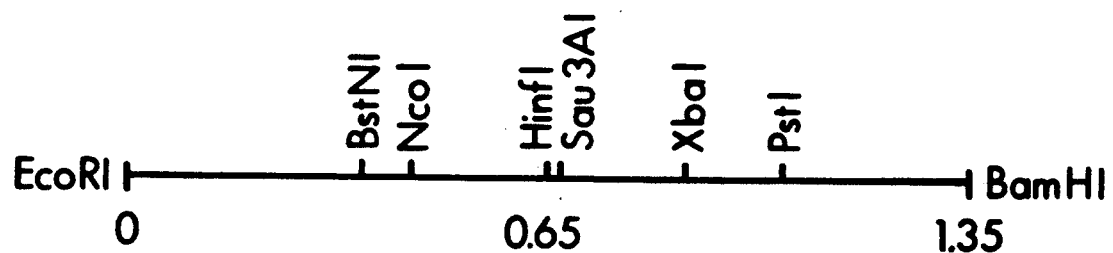
FIG. 6 shows the restriction map of pAC365.

A restriction map of pAC365 DNA was obtained using a standard method. The results of the mapping is shown in FIG. 6. The human sequence can be excised from the recombinant with EcoRI and BamHI in the form of a 1.35 kbp (approx.) fragment. The human sequence is flanked by 7 nucleotides on one end and 11 on the other both from the polylinker region of Bluescript. See FIG. 6.

Figure 7:
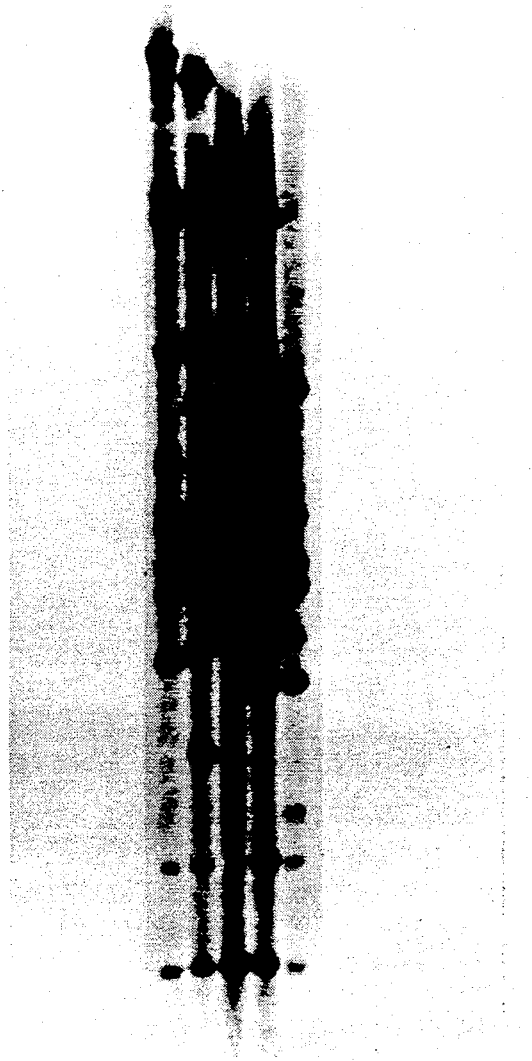
FIG. 7 shows the results of a hybridization blot where PstI digested human genomic DNA was probed with the insert of pAC365.

The 1.35 kbp fragment was excised and used to probe PstI digested human genomic DNA identically prepared as in Example 5, and under identical conditions. The results of the hybridization is shown in FIG. 7. A comparison of FIG. 5D with FIG. 7 shows that the signal patterns in the two blots were identical. This shows that the DNA sequence from Band 4 of FIG. 4 was successfully cloned into pAC365.

Figure 8:
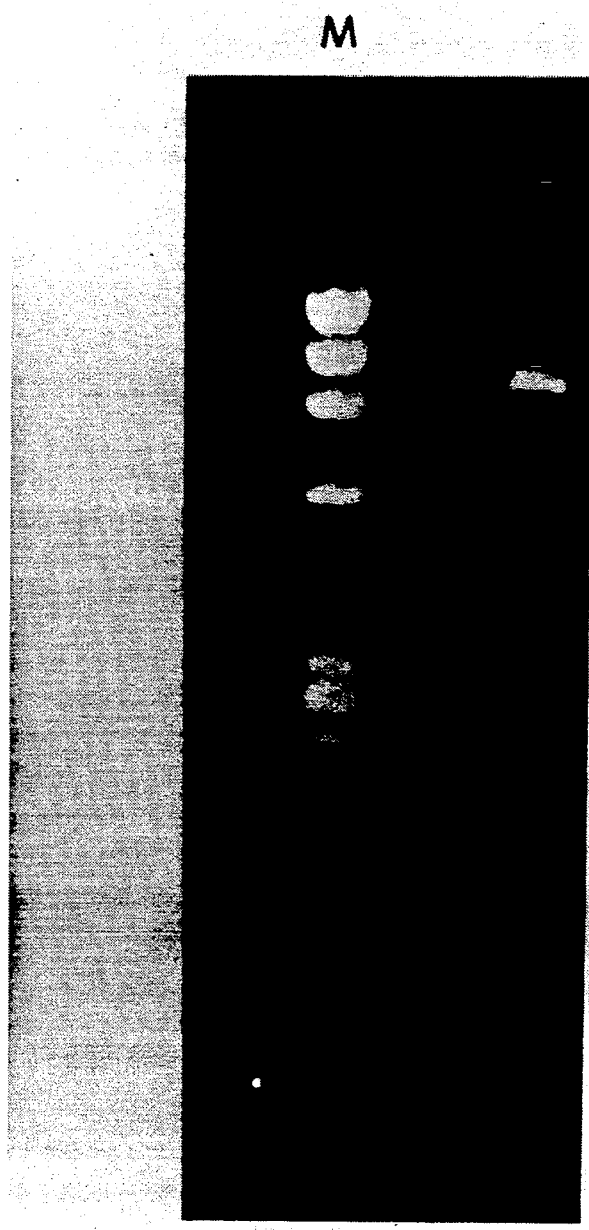
FIG. 8 shows the electrophoretic pattern of the restriction fragments produced by digesting the 1.35 kbp human insert of pAC365 with BstNI.

The 1.35 kbp fragment was digested with BstNI and the restriction digest was electrophoresed in a 3% Nu-Sieve agarose gel. [NuSieve is a trademarked product of FMC Corporation]. The electrophoretic pattern is shown in FIG. 8. Lane M of FIG. 8 contained phi-x HaeIII molecular weight markers. The BstNI digest of the 1.35 kbp fragment shows a broad band at about 70–100 bp (indicated by an arrow in the Figure) and a band at a higher molecular weight of approximately 0.9 kbp. The sum of the molecular weights pertaining to these two bands is below 1.35 kbp. Therefore, the results indicate that the 1.35 kbp fragment comprises several copies of an approximately 70–100 bp VTR "core" sequence.

Example 7

Analysis Of The Subfragments Of The pAC365 Insert

The 1.35 kbp human sequence cloned into pAC365 was excised from the plasmid along with 18 nucleotides from the polylinker region of Bluescript by digestion with EcoRI and BamHI. The excised fragment is further digested with one of the following enzymes: PstI, XbaI, Sau3A I, HinfI, and NcoI, thus generating five subfragments that each had the EcoRI site of 1.35 kbp fragment at one end.

Figure 9A:
FIG. 9 shows the results of a hybridization blot where PstI digested human genomic DNA was probed with the EcoRI-PstI (FIG. 9A) or the EcoRI-NcoI (FIG. 9B) subfragment of the 1.35 kbp human insert of pAC365.
Figure 9B:

Each of these five subfragments were tested for its utility as multi-locus, polymorphic probes. Each is hybridized to a replicate panel of PstI digested, unrelated, human genomic DNAs. The hybridization conditions were as described in Example 5. Parts of the results are shown in FIG. 9. FIGS. 9A, and 9B show the results where EcoRI-PstI, and EcoRI-NcoI subfragments respectively, were used as the probe. It is readily seen that each of these subfragments generated the same pattern as the full pAC365 insert. Compare FIG. 7 with FIGS.

9A, and 9B. Furthermore, the other subfragments also yielded the identical banding pattern. Hence, only the results for the largest (EcoRI-PstI) and the smallest (EcoRI-NcoI) subfragments are shown.

Finally, the DNA in the 100 bp area of FIG. 8 was used as probe, and was able to generate an identical pattern on a replicate panel of target human DNA. This is further evidence that pAC365 contains a VTR sequence.

This Example shows that each of these subfragments are useful multi-locus, polymorphic bands.

Example 8

Hybrid Formation And Stability Under High and Low Stringency Conditions

The 1.35 kbp insert of pAC365 was used to probe a panel of PstI digested human genomic DNA. The results are shown in FIG. 10. FIG. 10A shows a Southern blot where hybrid formation took place at 50° C., in 5 X SSPE, and the blot was washed at 65° C. in 2 X SSC. FIG. 10B shows a duplicate blot except it was washed at 65° C. in 0.1 X SSC. No unlabeled total human genomic DNA was added to the probe mix.

It is believed that the probe contained a small amount of Alu-like sequence, and this accounts for the background signal. More significantly, the background is dramatically lower in FIG. 10B than in FIG. 10A. Most importantly, the specific signals, i.e., the polymorphic bands are strong and unambiguous when the blot was washed under high stringency conditions.

Figure 10C:
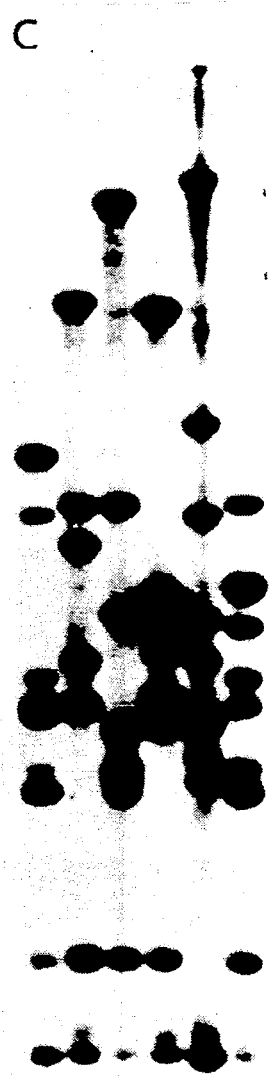
FIG. 10 shows the results of hybridization blots where PstI digested human genomic DNA was hybridized with the insert of pAC365 under (1) low associational stringency and low stringency wash (FIG. 10A); (2) low associational stringency and high stringency wash (FIG. 10B); and (3) high associational stringency and high stringency wash (FIG. 10C).

When hybrid formation and washing take place under more stringent conditions, background suppression is further improved. FIG. 10C shows a blot where hybrids were formed at 65° C. in 5 X SSPE, and where the blot was washed at 65° C. in 0.1 X SSC. The hybrids were actually stable at the even more stringent conditions: 0.01 X SSC at 65° C.

These results can be juxtaposed with those obtained using pAC256 as a probe. pAC256 is a Bluescript recombinant containing a human insert sequence which contains a Variable Tandem Repeat Sequence. See McClain et al., Am. J. of Human Genetics 41(Suppl.):A259 (1987). pAC256 behaves in conformity with prior art expectation. Prior art teaches that even though VTR probes can detect many loci at low stringency, the probes can only identify a single locus at high stringency. See, for example, Nakamura et al. (1987), Science 235: 1616, at 1618.

FIG. 11 illustrates just this point. Genomic human DNA were extracted, digested with PstI, and hybridized in the Southern format to pAC256 human insert at 65° C. in 5 X SSPE. FIG. 11A shows the results when the blot was washed at 65° C. in 2 X SSC. FIG. 11B shows the results when the blot was instead washed at 65° C. in 0.1 X SSC. It is readily seen that many of the bands detected under the less stringent conditions were unstable under the more stringent conditions and were washed away. The fact that no more than two bands were seen in each of the lanes containing target human DNA is consistent with the notion that at most a single locus—the locus from which the probe sequence originated—can be detected.

Example 9

Equivalency Of Various DNA Sequences As Polymorphic Probes

The following polynucleotide sequences were tested for differences, if any, in terms of the ability to detect polymorphism at multiple loci: DNA contained in Band C of FIG. 1A ("Band C DNA"); 19-MSP (defined below); the insert of pAC365; and the 5 subfragments described in Example 7.

19-MSP was obtained from "Band C DNA" by digesting the latter with MspI. "Band C DNA" appears to contain more than one species of DNA sequences of about 5 kbp. One species is cut into several smaller pieces by MspI. This species does not detect polymorphism. The other species is also cut by MspI, but the larger digestion product is only slightly smaller than 5 kbp. This approximately 5 kbp product is designated 19-MSP.

Figure 12A:
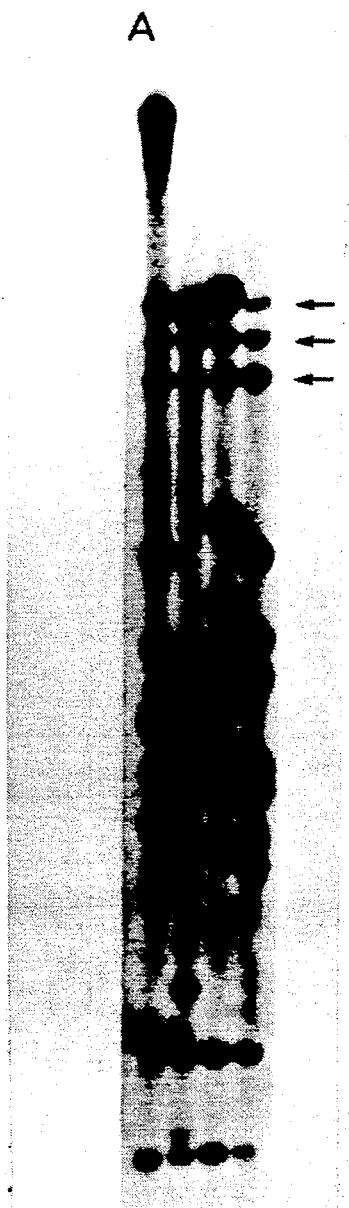
FIG. 12 shows the comparative banding patterns in hybridization blots where PstI digested human genomic DNA was probed with either "Band C DNA" (FIG. 12A), or with 19-MSP (FIG. 12B).
Figure 12B:
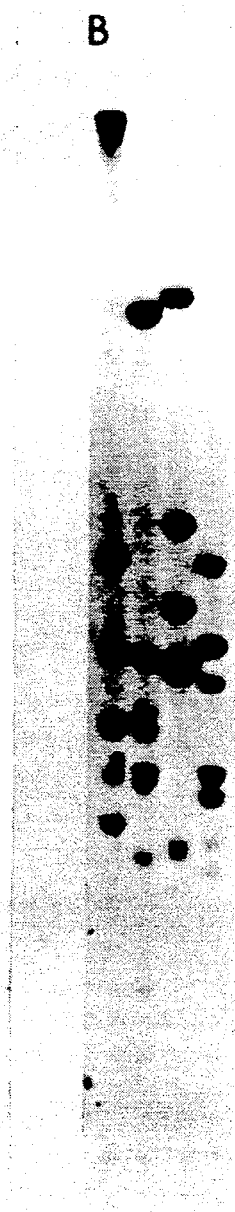

19-MSP and "Band C DNA" detected the same polymorphic bands when tested against genomic DNA from more than twenty genetically unrelated individuals. "Band C DNA" was able to detect, in addition to these polymorphic bands, several non-polymorphic bands. These results are illustrated in FIG. 12. FIGS. 12A and 12B show Southern blots probed respectively with "Band C DNA" and 19-MSP, but are otherwise prepared in duplicate. Each blot contained PstI digested genomic DNA from genetically unrelated individuals. When one of test lanes, for example, the rightmost test lane in FIG. 12A is compared with its counterpart, the rightmost test lane of FIG. 12B, it is seen that the former contain extra bands which are marked with arrows. However, these are non-polymorphic bands, as evidenced by the appearance of the same sized bands in all other test lanes in FIG. 12A. These results show that "Band C DNA" and 19-MSP recognize the same DNA polymorphisms.

19-MSP and the insert of pAC365 detected the same polymorphic bands when tested against genomic DNA from 107 genetically unrelated individuals. These results show that the insert of pAC365 and 19-MSP are equivalent probes.

Similarly, each of the five subfragments described in Example 7 have been shown to be equivalent to pAC365. (Representative data shown in FIGS. 7 and 9).

Example 10

Figure 13:
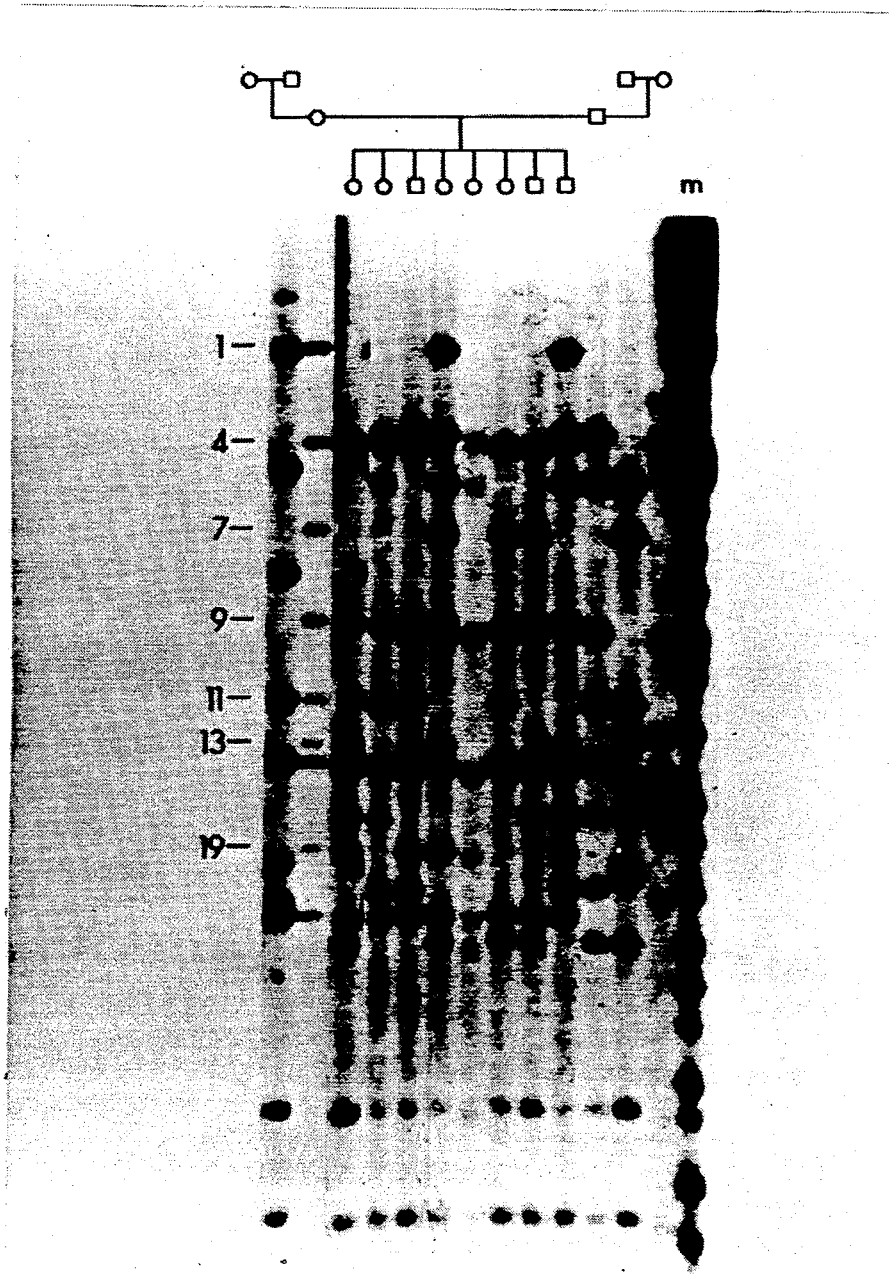
FIG. 13 shows the results of a hybridization blot where PstI digested genomic DNAs from a family spanning three generations were probed with the 1.35 kbp human insert of pAC365.

365 Detects Multiple Loci Which Segregate Independently In the Mendelian Fashion Genomic DNAs were extracted from individuals belonging to families spanning three generations, digested with PstI, and probed with pAC365 insert in the Southern Format. FIG. 13 shows the results of one such family study. The family tree at the top of the figure indicate the source of DNA in each of the test lanes. The lanes marked (m) contained molecular weight markers.

A total of 27 bands of varying sizes were detected by hybridization with pAC365. These are partially numbered on the side of the figure for identification. Table 1 shows the phenotype of each individual.

Several conclusions can be drawn from these results. First, each and every band which is present in any one of the eight children is also present in either the father or the mother. This result is consistent with stable chromosomal inheritance. Similarly, every band which is present in the father is present in either the paternal grandfather or grand-mother.

Second, the results are consistent with independent Mendelian segregation of alleles present on sister chromosomes. For example, Bands 1 and 4 appear to be two alleles to the same gene. The mother has both of these alleles, presumably one on each sister chromosome. However, each of the eight children inherits one or the other allele, but never both. Thus, the mode of inheritance is consistent with independent Mendelian segregation. Similarly, Bands 10 and 17 in the father segregate in a manner which is consistent with the notion that they are two alleles on the same gene.

Figure 14A:
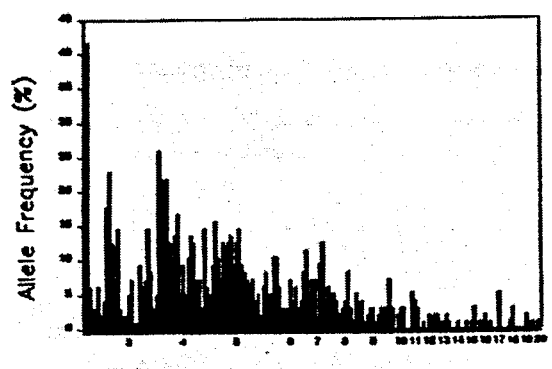
FIG. 14 shows the allelic distributions of genetic loci detectable by pAC365 in American Blacks (FIG. 14A), Caucasoids (FIG. 14B), and Hispanics (FIG. 14C).
Figure 14B:
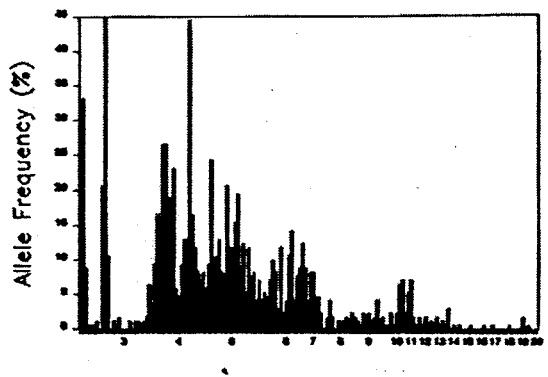
Figure 14C:
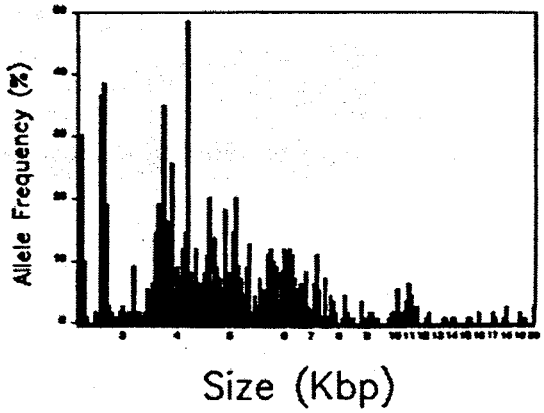

FIGS. 14A, 14B, and 14C show the distributions in American Blacks, Caucasoids, and Hispanics respectively. The y-axis is measured in per cent, and the x-axis is measured in kilobase pairs. The frequency distributions are more fully set forth in Table 2.

TABLE 1
Inheritance And Segregation Of Allele Within A Family*

| Family Member Bands | 1 | 2 | 3 | 4 | 5 | 6 | 7 | 8 |   |   |   |   |
|---|---|---|---|---|---|---|---|---|---|---|---|---|
| 1 | + | + | − | − | − | + | − | − | − | + | − | − | − |
| 2 | − | − | − | − | − | − | − | − | − | − | − | − | + |
| 3 | − | − | − | + | + | + | + | − | − | + | + | − | + |
| 4 | − | + | + | + | + | − | + | + | + | − | − | − | − |
| 5 | + | − | − | − | − | − | − | − | − | − | − | − | − |
| 6 | − | − | − | + | − | + | + | − | − | + | + | + | − |
| 7 | − | + | − | − | − | + | − | + | + | − | − | + | − |
| 8 | + | − | − | − | − | − | − | − | − | − | − | − | − |
| 9 | − | + | + | + | + | + | − | − | + | + | − | − | − |
| 10 | − | − | − | − | + | + | + | + | − | − | + | − | + |
| 11 | + | + | − | + | + | − | − | + | − | − | + | + | − |
| 12 | − | − | − | − | − | − | − | − | ± | − | − | + | + |
| 13 | − | + | + | − | − | + | − | − | − | + | − | − | − |
| 14 | + | + | + | + | + | + | + | + | + | + | + | − | + |
| 15 | − | − | − | − | − | − | − | − | − | − | − | + | − |
| 16 | − | − | − | − | − | − | − | − | − | − | − | − | + |
| 17 | − | − | + | + | − | − | − | − | + | +· | + | + | − |
| 18 | − | − | − | − | − | − | − | − | − | − | − | − | + |
| 19 | − | + | + | − | + | + | + | − | − | + | − | − | − |
| 20 | + | − | − | − | − | − | − | − | − | − | − | + | − |
| 21 | − | − | − | − | − | − | − | − | − | − | − | + | − |
| 22 | − | − | − | + | + | − | − | − | − | + | + | − | + |
| 23 | + | − | − | − | − | − | − | − | − | − | − | − | − |
| 24 | + | + | + | + | + | + | + | + | + | + | − | − | − |
| 25 | − | − | + | − | − | + | + | + | + | − | + | + | − |
| 26 | + | + | + | + | + | + | + | + | + | + | + | + | + |
| 27 | + | + | + | + | + | + | + | + | + | + | + | + | + |

*No data from maternal grandmother.

Third, the results are consistent with the notion that Band 1 is not linked to any of Band 7, 9, 13 or 19. These bands are all present in the mother. However, child #8 inherited Band 1, but not Band 7 from the mother. Therefore, Band 1 is not linked to Band 7. Child #1 inherited Bands 9, 13 and 19, but not Band 1 from the mother. Therefore, Band 1 is not linked to Band 9, 13 or 19.

Similar analyses lead to the conclusion that Band 7 is not linked to any of the other Bands present exclusively in the mother, nor Band 9, nor Band 13 and 19. Bands 1, 7, 9, 13 and 19 represent five genetic loci.

Example 11

Population Genetics and Allele Frequency

DNAs from 423 genetically unrelated individuals were tested in this study. Each DNA sample was digested with PstI and probed in a Southern hybridization procedure. For 127 samples, the insert from pAC365 was used as the probe. For the other 296 samples, 19-MSP was used as the probe. However, it had been established that the two probes recognize the same DNA polymorphisms. Therefore, pooling of results obtained by using these probes is valid. The pooled results have been sorted according to their ethnic origins (i.e., American Blacks, Caucasoids, and Hispanics). The frequency v. allele size distributions are shown in FIG. 14.

TABLE 2
Allele Frequencies For Three Racial Groups**

| | Fragment Size (kilobases)*** | | | | | | | | |
|---|---|---|---|---|---|---|---|---|---|
| | 2.25 | 2.30 | 2.35 | 2.40 | 2.45 | 2.50 | 2.55 | 2.60 | 2.65 |
| Blacks | 42 | 6 | 3 | 2 | 6 | 2 | 4 | 18 | 23 |
| Caucasoids | 33 | 9 | 1 | 1 | 1 | 1 | 0 | 21 | 45 |
| Hispanics | 30 | 10 | 1 | 0 | 0 | 2 | 1 | 37 | 39 |
| | 2.70 | 2.75 | 2.80 | 2.85 | 2.90 | 2.95 | 3.00 | 3.05 | |
| Blacks | 13 | 7 | 15 | 3 | 2 | 2 | 5 | 7 | |
| Caucasoids | 11 | 0 | 1 | 1 | 2 | 0 | 0 | 0 | |
| Hispanics | 19 | 3 | 2 | 1 | 1 | 2 | 3 | 1 | |
| | 3.10 | 3.15 | 3.20 | 3.25 | 3.30 | 3.35 | 3.40 | 3.45 | |
| Blacks | 1 | 1 | 9 | 6 | 7 | 15 | 8 | 3 | |
| Caucasoids | 1 | 0 | 1 | 1 | 1 | 1 | 2 | 7 | |
| Hispanics | 2 | 2 | 9 | 2 | 2 | 1 | 2 | 6 | |
| | 3.50 | 3.55 | 3.60 | 3.65 | 3.70 | 3.75 | 3.80 | 3.85 | |
| Blacks | 5 | 26 | 22 | 16 | 22 | 13 | 8 | 14 | |
| Caucasoids | 2 | 10 | 17 | 10 | 27 | 27 | 11 | 19 | |
| Hispanics | 3 | 6 | 15 | 19 | 17 | 35 | 17 | 15 | |
| | 3.90 | 3.95 | 4.00 | 4.05 | 4.10 | 4.15 | 4.20 | 4.25 | 4.3 |
| Blacks | 17 | 5 | 9 | 5 | 10 | 14 | 13 | 7 | 7 |
| Caucasoids | 23 | 6 | 5 | 10 | 13 | 13 | 44 | 17 | 12 |

TABLE 2-continued

Allele Frequencies For Three Racial Groups**
Fragment Size (kilobases)***

| | | | | | | | | | |
|---|---|---|---|---|---|---|---|---|---|
| soids | | | | | | | | | |
| Hispanics | 26 | 6 | 9 | 7 | 12 | 15 | 49 | 8 | 6 |

| | 4.35 | 4.40 | 4.45 | 4.50 | 4.55 | 4.60 | 4.65 | 4.70 | 4.75 |
|---|---|---|---|---|---|---|---|---|---|
| Blacks | 3 | 15 | 6 | 5 | 9 | 16 | 10 | 7 | 13 |
| Caucasoids | 8 | 7 | 8 | 6 | 10 | 24 | 8 | 11 | 13 |
| Hispanics | 12 | 6 | 6 | 8 | 11 | 20 | 6 | 14 | 9 |

| | 4.80 | 4.85 | 4.90 | 4.95 | 5.00 | 5.05 | 5.10 | 5.15 | 5.20 |
|---|---|---|---|---|---|---|---|---|---|
| Blacks | 10 | 13 | 14 | 9 | 13 | 15 | 9 | 8 | 7 |
| Caucasoids | 8 | 8 | 21 | 12 | 12 | 15 | 20 | 9 | 12 |
| Hispanics | 7 | 6 | 18 | 8 | 8 | 15 | 20 | 9 | 7 |

| | 5.25 | 5.30 | 5.35 | 5.40 | 5.45 | 5.50 | 5.55 | 5.60 | 5.65 |
|---|---|---|---|---|---|---|---|---|---|
| Blacks | 6 | 7 | 4 | 5 | 2 | 6 | 8 | 5 | 5 |
| Caucasoids | 5 | 12 | 8 | 8 | 4 | 7 | 4 | 5 | 5 |
| Hispanics | 5 | 9 | 13 | 2 | 5 | 3 | 7 | 6 | 6 |

| | 5.70 | 5.75 | 5.80 | 5.85 | 5.90 | 5.95 | 6.0 | 6.1 | 6.2 |
|---|---|---|---|---|---|---|---|---|---|
| Blacks | 10 | 10 | 6 | 3 | 3 | 3 | 7 | 4 | 6 |
| Caucasoids | 7 | 10 | 8 | 3 | 12 | 2 | 4 | 11 | 14 |
| Hispanics | 11 | 12 | 10 | 9 | 4 | 8 | 12 | 10 | 12 |

| | 6.3 | 6.4 | 6.5 | 6.6 | 6.7 | 6.8 | 6.9 | 7.0 | 7.1 |
|---|---|---|---|---|---|---|---|---|---|
| Blacks | 3 | 4 | 8 | 12 | 5 | 7 | 7 | 1 | 9 |
| Caucasoids | 4 | 8 | 9 | 12 | 9 | 4 | 8 | 8 | 5 |
| Hispanics | 11 | 7 | 6 | 6 | 6 | 8 | 3 | 2 | 6 |

| | 7.2 | 7.3 | 7.4 | 7.5 | 7.6 | 7.7 | 7.8 | 7.9 | 8.0 |
|---|---|---|---|---|---|---|---|---|---|
| Blacks | 13 | 4 | 6 | 5 | 5 | 4 | 2 | 3 | 4 |
| Caucasoids | 5 | 2 | 0 | 2 | 4 | 2 | 0 | 1 | 1 |
| Hispanics | 11 | 6 | 1 | 7 | 1 | 5 | 4 | 2 | 0 |

| | 8.1 | 8.2 | 8.3 | 8.4 | 8.5 | 8.6 | 8.7 | 8.8 | 8.9 |
|---|---|---|---|---|---|---|---|---|---|
| Blacks | 8 | 3 | 1 | 5 | 3 | 4 | 1 | 2 | 3 |
| Caucasoids | 1 | 2 | 1 | 2 | 2 | 1 | 1 | 2 | 2 |
| Hispanics | 1 | 5 | 2 | 1 | 1 | 0 | 0 | 4 | 1 |

| | 9.0 | 9.1 | 9.2 | 9.3 | 9.4 | 9.5 | 9.6 | 9.7 | 9.8 |
|---|---|---|---|---|---|---|---|---|---|
| Blacks | 3 | 1 | 2 | 3 | 3 | 3 | 7 | 3 | 0 |
| Caucasoids | 2 | 1 | 2 | 4 | 1 | 2 | 1 | 1 | 2 |
| Hispanics | 1 | 2 | 2 | 1 | 1 | 0 | 0 | 0 | 1 |

| | 9.9 | 10 | 10.2 | 10.4 | 10.6 | 10.8 | 11.0 | 11.2 | 11.4 |
|---|---|---|---|---|---|---|---|---|---|
| Blacks | 2 | 3 | 3 | 0 | 0 | 5 | 4 | 3 | 0 |
| Caucasoids | 1 | 2 | 7 | 7 | 2 | 5 | 7 | 2 | 1 |
| Hispanics | 2 | 2 | 6 | 2 | 2 | 4 | 6 | 5 | 3 |

| | 11.6 | 11.8 | 12.0 | 12.2 | 12.4 | 12.6 | 12.8 | 13.0 | 13.2 |
|---|---|---|---|---|---|---|---|---|---|
| Blacks | 1 | 0 | 2 | 1 | 2 | 2 | 1 | 1 | 2 |
| Caucasoids | 2 | 1 | 2 | 1 | 1 | 1 | 2 | 1 | 1 |
| soids | | | | | | | | | |
| Hispanics | 3 | 0 | 0 | 1 | 2 | 0 | 0 | 0 | 0 |

| | 13.4 | 13.6 | 13.8 | 14.0 | 14.2 | 14.4 | 14.6 | 14.8 | 15.0 |
|---|---|---|---|---|---|---|---|---|---|
| Blacks | 1 | 0 | 0 | 1 | 0 | 0 | 1 | 0 | 1 |
| Caucasoids | 1 | 3 | 0 | 1 | 0 | 1 | 0 | 0 | 0 |
| Hispanics | 1 | 1 | 0 | 1 | 1 | 0 | 0 | 0 | 0 |

| | 15.2 | 15.4 | 15.6 | 15.8 | 16.0 | 16.2 | 16.4 | 16.6 | 16.8 |
|---|---|---|---|---|---|---|---|---|---|
| Blacks | 3 | 0 | 1 | 1 | 2 | 0 | 1 | 0 | 0 |
| Caucasoids | 1 | 0 | 0 | 0 | 0 | 1 | 0 | 0 | 1 |
| Hispanics | 1 | 1 | 0 | 0 | 2 | 0 | 0 | 0 | 0 |

| | 17.0 | 17.2 | 17.4 | 17.6 | 17.8 | 18.0 | 18.2 | 18.4 |
|---|---|---|---|---|---|---|---|---|
| Blacks | 5 | 0 | 0 | 0 | 1 | 3 | 0 | 0 |
| Caucasoids | 0 | 0 | 0 | 0 | 0 | 1 | 0 | 0 |
| Hispanics | 2 | 1 | 0 | 0 | 1 | 3 | 0 | 0 |

| | 18.6 | 18.8 | 19.0 | 19.2 | 19.4 | 19.6 | 19.8 | 20.0 |
|---|---|---|---|---|---|---|---|---|
| Blacks | 0 | 0 | 2 | 0 | 1 | 0 | 1 | 1 |
| Caucasoids | 0 | 0 | 2 | 0 | 1 | 0 | 0 | 0 |
| Hispanics | 0 | 0 | 2 | 0 | 1 | 0 | 0 | 3 |

**Allele frequencies are stated in percent in Table 2.
***The standard error for fragment size is approximately 0.6% of the size of the fragment. Therefore, DNA fragments whose sizes are within 2% of each other (3 standard deviations) are considered indistinguishable.

Example 12

Characterization of pAC365

Genomic DNA from various human cell lines was extracted, digested with PstI, and hybridized with pAC365 insert in the Southern format. 7024, 7351, 7047, 7432, 7433 and 7015 were obtained from Centre d'Etude du Polymorphisme Humain in France. 1202 was obtained from the National Institute of General Medical Sciences (NIGMS) Human Genetic Cell Repository (Catalog Number 1202B). It is a lymphoblast cell line with 49 chromosomes (XXXXY). CEM and Jurket are T lymphoblastoid cell lines. K562 is a erythroleukemia cell line and HL60 is a promyelocytic cell line. CEM, K562, and HL60 can be obtained from the American Type Culture Collection ("ATCC") under ATCC catalog numbers CCL119, CCL243, and CCL240, respectively.

The bands detected in the Southern blot are set forth in Table 3 below. For example, pAC365 insert detected 9 bands ranging from 7.1 kilobase pairs to 2.2 kilobase pairs when hybridized with PstI digested K562 cell DNA. The banding pattern obtained for each cell line is unique. Therefore, when used for probe purposes polynucleotide sequences can be characterized, or "fingerprinted" by the banding pattern with known target DNA.

TABLE 3

"Fingerprint" of pAC365

| 7024 | 7351 | CEM | 1202 | HL60 | Jur. | 7047 | 7432 | 7433 | 7015 | K562 |
|---|---|---|---|---|---|---|---|---|---|---|
| 6.3# | 6.5 | 20 | 11 | 10.7 | 10.6 | 9.6 | 9.7 | 9.3 | 6.5 | 7.1 |
| 5.3 | 5.6 | 7.7 | 6.3 | 6.6 | 5.2 | 9.2 | 9.3 | 5.7 | 5.7 | 6.2 |
| 4.9 | 5.3 | 6.1 | 5.8 | 5.0 | 5.1 | 7.1 | 6.4 | 5.6 | 5.4 | 4.4 |
| 4.4 | 5.0 | 5.0 | 4.6 | 4.6 | 4.9 | 5.7 | 5.7 | 5.1 | 4.9 | 4.2 |

TABLE 3-continued

| | | | | "Fingerprint" of pAC365 | | | | | | |
|---|---|---|---|---|---|---|---|---|---|---|
| 7024 | 7351 | CEM | 1202 | HL60 | Jur. | 7047 | 7432 | 7433 | 7015 | K562 |
| 4.2 | 4.9 | 4.6 | 4.2 | 4.5 | 4.7 | 5.4 | 5.4 | 4.9 | 4.4 | 4.1 |
| 3.7 | 4.2 | 4.1 | 2.6 | 4.3 | 4.3 | 5.2 | 5.2 | 4.2 | 4.1 | 3.7 |
| 3.6 | 4.1 | 4.0 | 2.3 | 3.8 | 4.2 | 4.9 | 5.1 | 3.8 | 3.6 | 3.6 |
| 2.6 | 3.8 | 3.8 | 2.2 | 3.5 | 4.0 | 4.7 | 4.7 | 3.7 | 2.6 | 2.6 |
| 2.3 | 2.6 | 3.6 | | 2.6 | 2.6 | 4.2 | 4.6 | 2.6 | 2.2 | 2.2 |
| 2.2 | 2.2 | 2.3 | | 2.2 | 2.3 | 3.9 | 3.6 | 2.2 | | |
| | | 2.2 | | | 2.2 | 3.7 | 2.6 | | | |
| | | | | | | 2.7 | 2.2 | | | |
| | | | | | | 2.2 | | | | |

Sizes of the fragments detected are stated in kbp in Table 3.

Example 13

Paternity Testing and Forensic Testing

Genomic DNAs were extracted from a child, the mother of the child and the alleged father. The DNAs were digested with PstI, electrophoresed and transferred for Southern hybridization. The DNA targets were probed with 19-MSP. FIG. 15A shows the results of the blot. Lanes labeled (m) contained molecular weight markers. Lanes (a), (b), and (c) contained DNA from the mother, the child, and the alleged father of the child respectively. Lane (d) contained a mixture of the child's DNA and the alleged father's DNA. The last lane often helps to resolve ambiguity whenever a band detected in the child's lane is close in size to a band detected in the alleged father's lane. In such a case, the presence of a singlet band in the relevant size region in the "child plus alleged father" lane would tend to indicate a common allele; and a doublet band would indicate distinct alleles.

FIG. 15A shows that at least 5 bands in lane (b) were not inherited from the mother because they are not present in lane (a). However, each of these bands (marked with arrows) are present in lane (b). Therefore, the evidence supports the theory that the alleged father is indeed the biological father.

DNAs were extracted from a rape victim, semen found on the victim and from a suspect of the crime. The DNAs were digested with PstI, and subjected to the Southern hybridization procedure. 19-MSP was used as a probe. FIG. 15B shows the results of the hybridization blot. Lane (a) contained DNA from the victim. Lane (b) and (c) contained DNA from semen found on the victim, and from a suspect, respectively. At least 8 bands (marked with arrows) in lane (b) do not match the bands in lane (a), clearly indicating that these bands did not arise from cells of the victim which somehow contaminated the semen sample. However, all 8 bands matched bands of the same sizes in lane (c). Therefore, the evidence that the semen came from the suspect was exceedingly strong.

Example 14

Relationships Among The Polymorphic Probes Of The Invention

Figure 16:
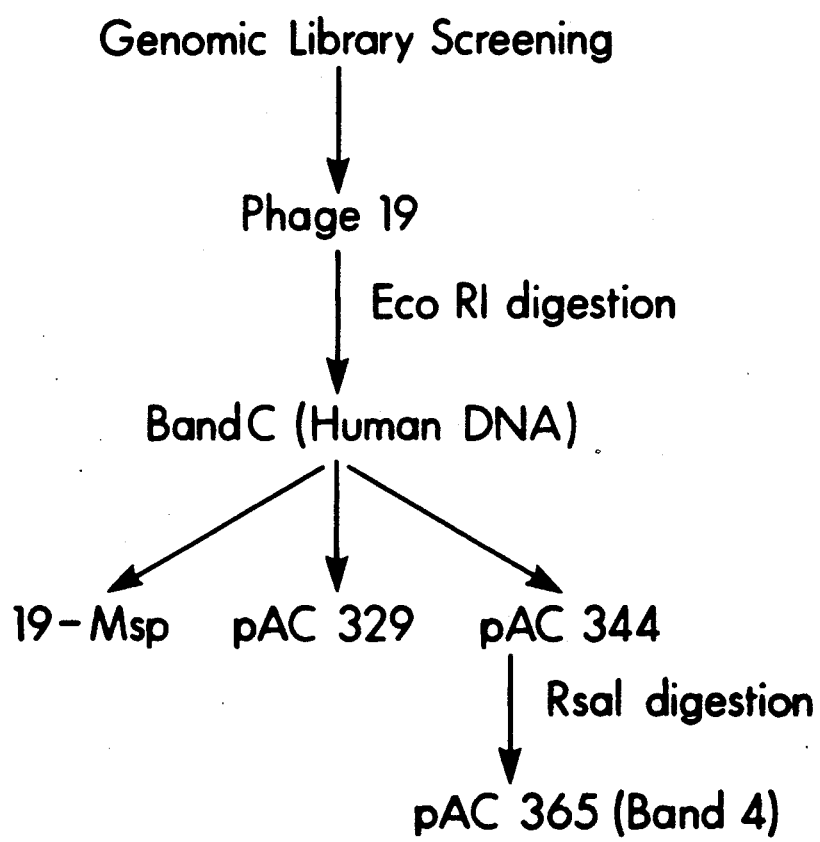
FIG. 16 shows the relationships among the human sequences of the invention.

FIG. 16 shows the relationships among the various DNA sequences of the present invention, which are useful as polymorphic probes.

DEPOSIT OF MICROORGANISM

Many polynucleotide sequences may be used to practice the present invention. Exemplary of such sequences are human genomic sequences which have been cloned into recombinant plasmids designated pAC329, pAC344, and pAC365. FIG. 16 shows the relationships among the cloned sequences of this invention.

An *E. coli* strain HB101 carrying the plasmid pAC329, an *E. coli* strain HB101 carrying the plasmid pAC344, and an *E. coli* strain HB101 carrying the pAC365 plasmid have been deposited with the Agricultural Research Culture Collection (NRRL), Peoria, IL, on Sep. 2, 1988, and have been assigned accession numbers NRRL B-18403, NRRL B-18404, and NRRL B-18405, respectively.

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

*E. coli* HB101 is available from the NRRL repository where its accession number is NRRL B-11371. Plasmids can be isolated from the *E. coli* host by use of standard procedures, e.g., using cleared lysate-isopycnic density gradient procedures, and the like.

The present invention is not to be limited in scope by the microorganisms deposited, since the deposited embodiment is intended as a single illustration of one aspect of the invention. Many variations of this invention as herein set forth may be made without departing from the spirit and scope thereof. The specific embodiments described are given by way of example only, and the invention is limited only by the terms of the appended claims.

We claim:

1. A polynucleotide sequence which forms stable hybrids under high stringency conditions with genomic Variable Tandem Repeat DNA sequences at multiple, polymorphic loci of a human, wherein said high stringency conditions comprise an aqueous environment containing about 0.1 x SSC, or less, at about 65° C., and wherein said polynucleotide sequence is selected from the group consisting of:
   (a) the human DNA insert in pAC329;
   (b) the human DNA insert in pAC344;
   (c) the human DNA insert in pAC365; and
   (d) mutational, insertional, or deletional variants of (a)–(d), wherein said variants form stable hybrids, under high stringency conditions, with DNA sequences which hybridize with said polynucleotide sequences of (a)–(d) above.

2. The polynucleotide sequence of claim 1, which is the human DNA insert in pAC329.

3. The polynucleotide sequence of claim 1 represented by the human DNA insert in pAC344.

4. The polynucleotide sequence of claim 1 which is the human DNA insert pAC365.

5. A recombinant vector having a polynucleotide sequence of any one of the claim 1.

6. A polynucleotide probe consisting of a polynucleotide sequence of claim 1 which has been labeled.

7. A method of genetic analysis comprising:
   (a) digesting a DNA sample with a restriction endonuclease;
   (b) separating the DNA restriction frequency according to size by electrophoresis;
   (c) transferring the separated DNA to a binding surface;
   (d) hybridizing the transferred DNA with a polynucleotide probe wherein said probe is a probe of claim 6; and
   (e) detecting the signals generated; whereby the pattern of signals generated provides information about the composition of the DNA sample.

* * * * *

UNITED STATES PATENT AND TRADEMARK OFFICE
CERTIFICATE OF CORRECTION

PATENT NO. : 5,206,137

DATED : April 27, 1993

INVENTOR(S) : Nancy Y. Ip and Howard J. Baum

It is certified that error appears in the above-identified patent and that said Letters Patent is hereby corrected as shown below:

Column 16  line 44: "365 Detects Multiple Loci" should read --pAC365 Detects Multiple Loci--.

Column 24, line 10: "restriction frequency" should read --restriction fragments--.

Signed and Sealed this

Fifteenth Day of February, 1994

Attest:

BRUCE LEHMAN

Attesting Officer    Commissioner of Patents and Trademarks